United States Patent
Janz et al.

(10) Patent No.: US 7,778,499 B2
(45) Date of Patent: Aug. 17, 2010

(54) SILICON PHOTONIC WIRE WAVEGUIDE BIOSENSOR

(75) Inventors: Siegfried Janz, Ottawa (CA); Pavel Cheben, Ottawa (CA); Andre Delage, Ottawa (CA); Adam Densmore, Orleans (CA); Dan-Xia Xu, Ottawa (CA)

(73) Assignee: National Research Council of Canada, Ottawa (CA)

( * ) Notice: Subject to any disclaimer, the term of this patent is extended or adjusted under 35 U.S.C. 154(b) by 108 days.

(21) Appl. No.: 11/898,660

(22) Filed: Sep. 13, 2007

(65) Prior Publication Data
US 2008/0292236 A1 Nov. 27, 2008

(51) Int. Cl.
G02B 6/00 (2006.01)
(52) U.S. Cl. .......................................... 385/12; 385/132
(58) Field of Classification Search .................... 385/12
See application file for complete search history.

(56) References Cited

U.S. PATENT DOCUMENTS

| | | | |
|---|---|---|---|
| 7,095,010 B2 * | 8/2006 | Scherer et al. | 250/227.11 |
| 7,336,859 B2 * | 2/2008 | Sanders | 385/12 |
| 2005/0078903 A1 * | 4/2005 | Grace et al. | 385/12 |
| 2005/0201660 A1 * | 9/2005 | Grot et al. | 385/12 |
| 2007/0269901 A1 * | 11/2007 | Armani et al. | 436/172 |
| 2008/0131049 A1 * | 6/2008 | Koch et al. | 385/12 |

FOREIGN PATENT DOCUMENTS

JP 06281568 A * 10/1994

OTHER PUBLICATIONS

Densmore et al., A Silicon-on-Insulator Photonic Wire Based Evanescent Field Sensor, Dec. 1, 2006, IEEE Photonics Technology Letters, vol. 18, No. 23, pp. 2520-2522.*

* cited by examiner

*Primary Examiner*—Sarah Song
(74) *Attorney, Agent, or Firm*—Brion Raffoul

(57) ABSTRACT

Methods and devices relating to a sensor for use in detecting and monitoring molecular interactions. A silicon waveguide sensing element is provided along with a layer of silicon. A silicon oxide layer is also provided between the waveguide element and the layer of silicon. The sensing element is adjacent to an aqueous solution in which the molecular interactions are occurring. A light beam travelling in the silicon waveguide creates an evanescent optical field on the surface of the sensing element adjacent to the boundary between the sensing element and the aqueous medium. Molecular interactions occurring on this surface affect the intensity or the phase of the light beam travelling through the waveguide by changing the effective refractive index of the medium. By measuring the effect on the intensity, phase, or speed of the light beam, the molecular interactions can be detected and monitored in real time.

12 Claims, 8 Drawing Sheets

SILICON PHOTONIC WIRE WAVEGUIDE BIOSENSOR

FIELD OF THE INVENTION

The present invention relates to sensor technology. More specifically, the present invention relates to sensors for detecting and quantifying molecular interactions by determining how much of an effect these molecular interactions have on characteristics of light passing through a waveguide adjacent an aqueous medium where these interactions are occurring.

BACKGROUND TO THE INVENTION

The recent increase in interest in and funding for the biochemical and pharmaceutical fields has created a need for more sensitive sensors that can detect and quantify molecular interactions. The detection of these molecular interactions determine whether chemical and biological processes are at work and, as such, are key to finding new and more effective pharmaceuticals.

Unfortunately, current biosensor technology suffers from a fragility and scarcity of the equipment. Current sensor technology, such as surface plasmon resonance (SPR), is quite well-known but the equipment requires delicate handling by technicians. Furthermore, such current technologies have sensitivities that are less then desirable. With SPR, the sensitivity of the equipment is limited by the short propagation length of the plasmon.

There is therefore a need for methods and devices that mitigate if not overcome the shortcomings of the prior art. Specifically, there is a need for techniques and devices which are easy to implement, robust, and whose sensitivity is not determined by the short propagation lengths of plasmons.

SUMMARY OF THE INVENTION

The present invention provides methods and devices relating to a sensor for use in detecting and monitoring molecular interactions. A silicon waveguide sensing element is provided along with a layer of silicon. A silicon oxide layer is also provided between the waveguide element and the layer of silicon. The sensing element is adjacent to an aqueous solution in which the molecular interactions are occurring. A light beam travelling in the silicon waveguide creates an evanescent optical field on the surface of the sensing element adjacent to the boundary between the sensing element and the aqueous medium. Molecular interactions occurring on this surface affect the intensity or the phase of the light beam travelling through the waveguide by changing the effective refractive index of the medium. By measuring the effect on the intensity, phase, or speed of the light beam, the molecular interactions can be detected and monitored in real time.

In one aspect, the present invention provides a sensor for use in detecting molecules in a liquid or gas medium, the sensor comprising:

a substrate layer, a light waveguide sensor element adjacent said medium a lower cladding layer between said sensor element and said substrate layer wherein molecular interactions at the waveguide surface affect at least one characteristic of light travelling through said waveguide sensor element.

In another aspect, the present invention provides a method for detecting molecular interactions in a medium using a sensor having a light waveguide sensor element adjacent said aqueous medium, the method comprising:

determining characteristics of light prior to said light entering said sensor element passing light through said sensor element determining characteristics of light after it has exited said sensor element comparing results of steps a) and c) to determine if changes in characteristics of said light occurred in the event said changes in characteristics occurred, measuring said changes wherein a presence of molecular interactions in said medium affect at least one characteristic of said light.

BRIEF DESCRIPTION OF THE FIGURES

The invention will be described with reference to the accompanying drawings, wherein.

DETAILED DESCRIPTION

Figure 1:
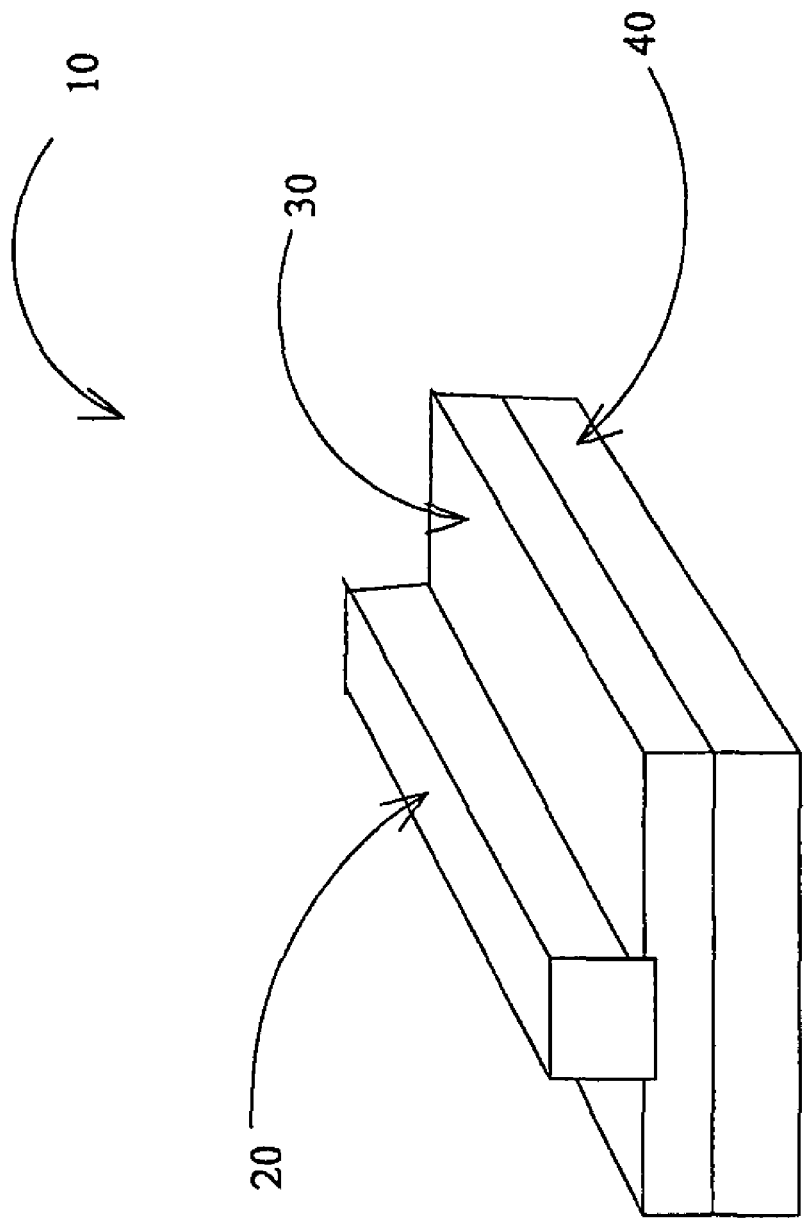
FIG. 1 is an isometric view of a sensor according to one aspect of the invention.

Referring to FIG. 1, a sensor 10 according to one aspect of the invention is illustrated. The sensor 10 has an optical waveguide 20 (a sensor element) on top of a silicon dioxide layer 30. The silicon dioxide layer 20 (a lower cladding layer) is sandwiched between the waveguide 20 and a silicon substrate 40.

Figure 2:
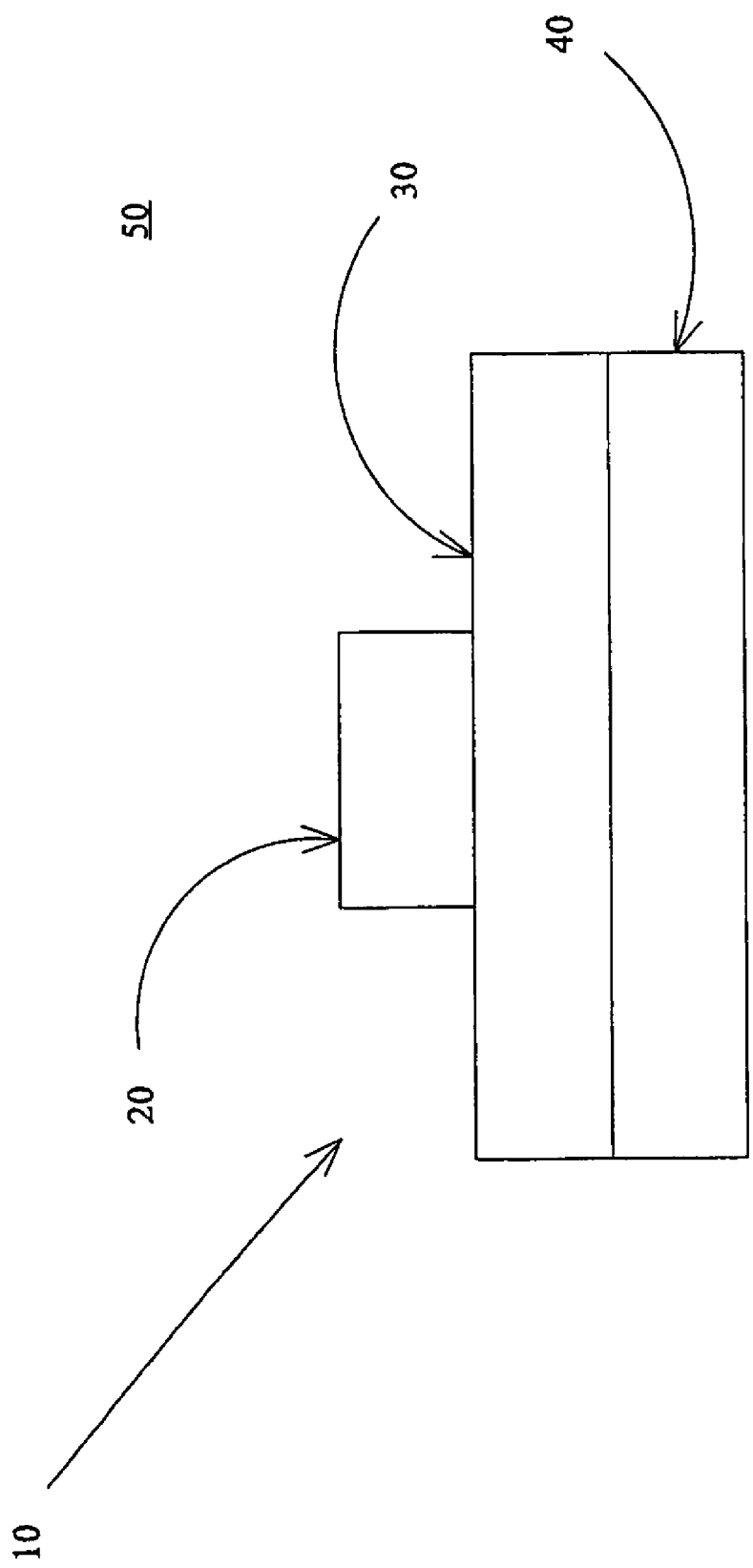
FIG. 2 is a front cut-away view of the sensor of FIG. 1 illustrating the core of the waveguide.

Referring to FIG. 2, an end cut-away view of the sensor 10 is illustrated. In use, from FIG. 2, a solution 50 (which may be water based) is adjacent the waveguide 20. The 50 contains the chemical or biochemical materials whose interactions are to be monitored or detected.

The sensor detects molecular interactions (or the presence of specific molecules) by having light passed through the sensor. The sensor detects the binding of specific, target molecules to receptor molecules on the waveguide surface. By detecting this binding, the presence of the target molecules is determined. The receptor molecules are previously attached (perhaps as a layer) to the waveguide surface. As an example, an antibody can be fixed to the sensor surface (the waveguide surface) to functionalize the antibody for detecting the presence of the corresponding antigen.

Figure 3:
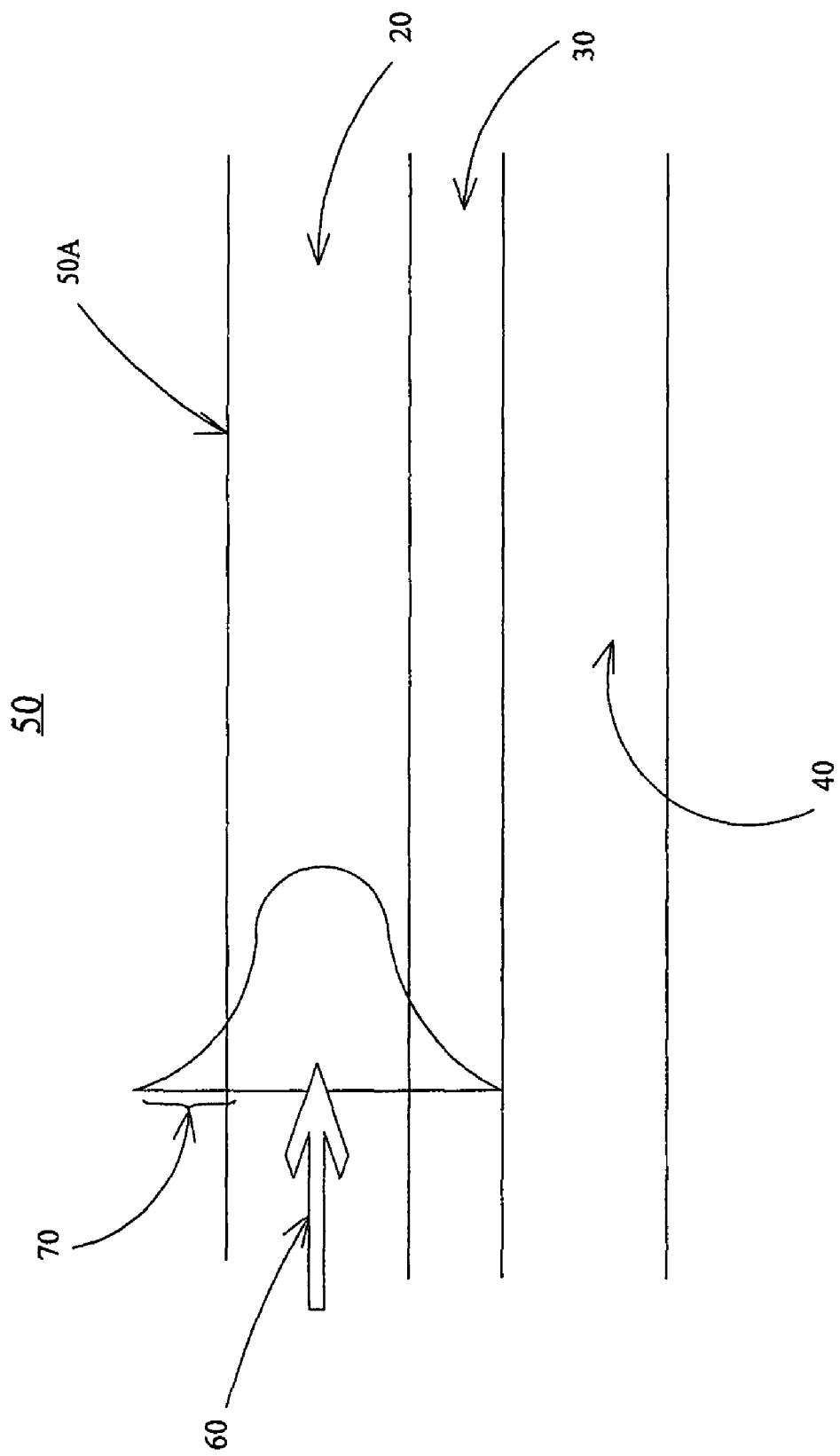
FIG. 3 is a side cut-away view of the sensor of FIG. 1 illustrating the direction of propagation of light travelling in the waveguide and the evanescent optical field produced by such light.

Referring to FIG. 3, a side-cutaway view of the sensor is illustrated. The sensor 20 operates by detecting the effect of target molecules binding to the waveguide surface on the characteristics of light as the light travels through the waveguide.

As is well-known in the art, especially to those well-versed in SPR technology, target molecules are detected when they bind to the surface 50A of the sensor. Light travelling in the waveguide 20 (in the direction 60 of propagation) produces an evanescent optical field 70 on the surface of the waveguide 20. The molecular interactions occurring near or at the surface 50A affect the refractive index of the liquid solution, thereby slowing down or delaying the light travelling through the waveguide. This effectively changes the speed and other characteristics of the light in the waveguide. Characteristics such as the intensity and the phase of the light are affected by the extent and number of molecular interactions on the surface of the waveguide.

Molecular interactions, such as the adsorption of molecules onto the sensor surface affect the speed of light as well as the attenuation of the light. The attenuation of the light also depends on the absorption cross section at the optical wavelength of the light travelling in the waveguide. As noted above, a phase change in the light in the waveguide may also be induced due to the adsorption of a molecular layer on the surface of the waveguide.

The changes in the characteristic of the light in the waveguide can be detected and measured by the use of well-known devices and techniques. Such devices as Mach-Zehnder interferometers and resonators may be used to measure these changes in characteristic. These same devices may be used to determine the initial characteristics of the light prior to their entering the sensor. Once the initial characteristics of the light are determined, these can be compared to the characteristics of the light after the light has passed through the sensor. The differences between these two sets of characteristics (such as speed of light, phase, etc.) would indicate the presence and number of molecular interactions detected.

Figure 4:
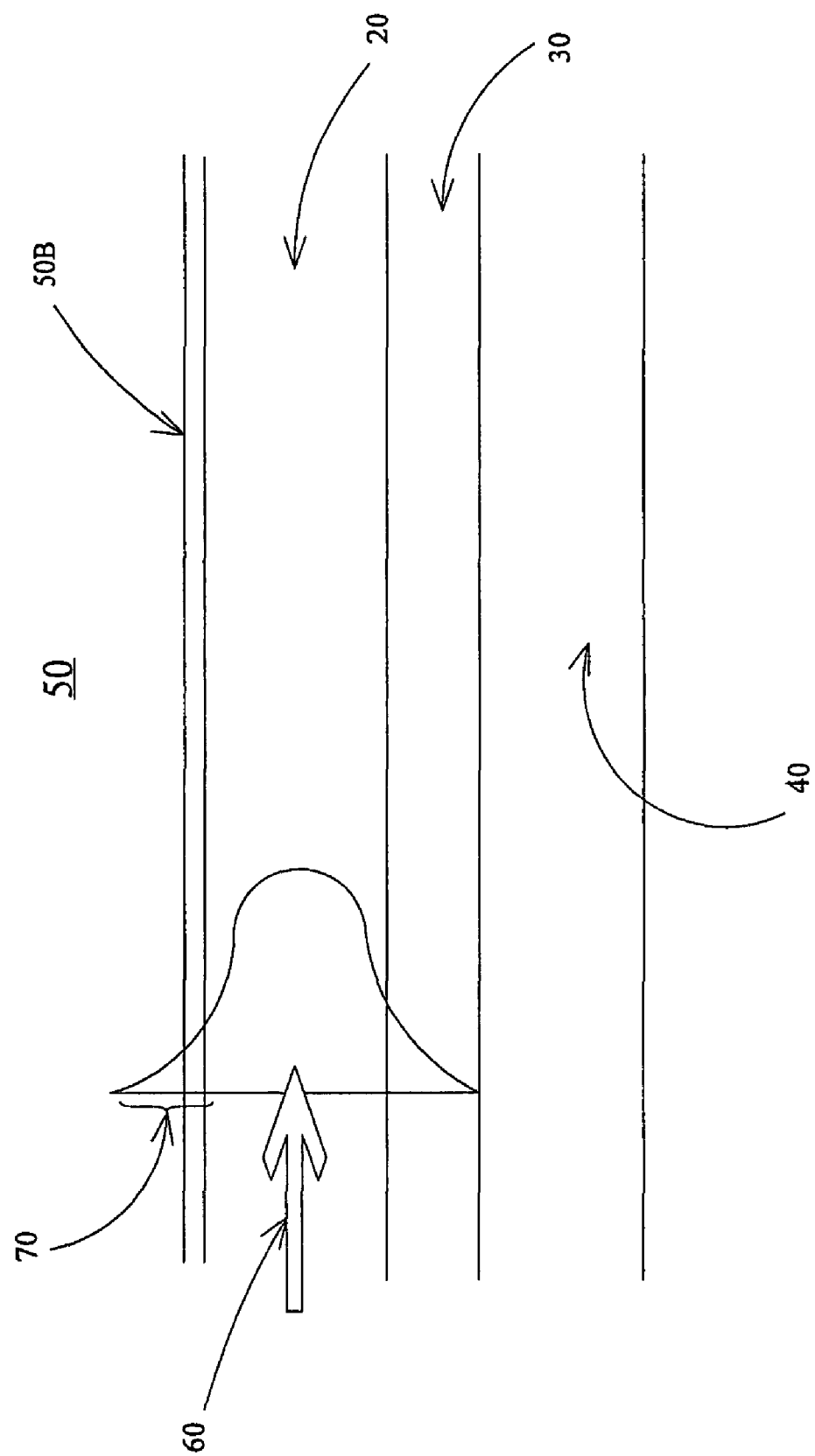
FIG. 4 illustrates the positioning of a molecular layer on a surface of the sensor of FIG. 1

Referring to FIG. 4, another cross-sectional view of the sensor is illustrated. As can be seen, the molecular layer 50B forms between the surface of the waveguide and the aqueous medium. Experiments have shown that sensor response increases with active sensor length and that sensor response increases with mode intensity at the perturbation location (i.e. the target molecule layer). The presence and number of target molecules can therefore be determined by sampling the characteristics (e.g. attenuation, phase, etc.) of the light travelling in the waveguide.

Figure 5:
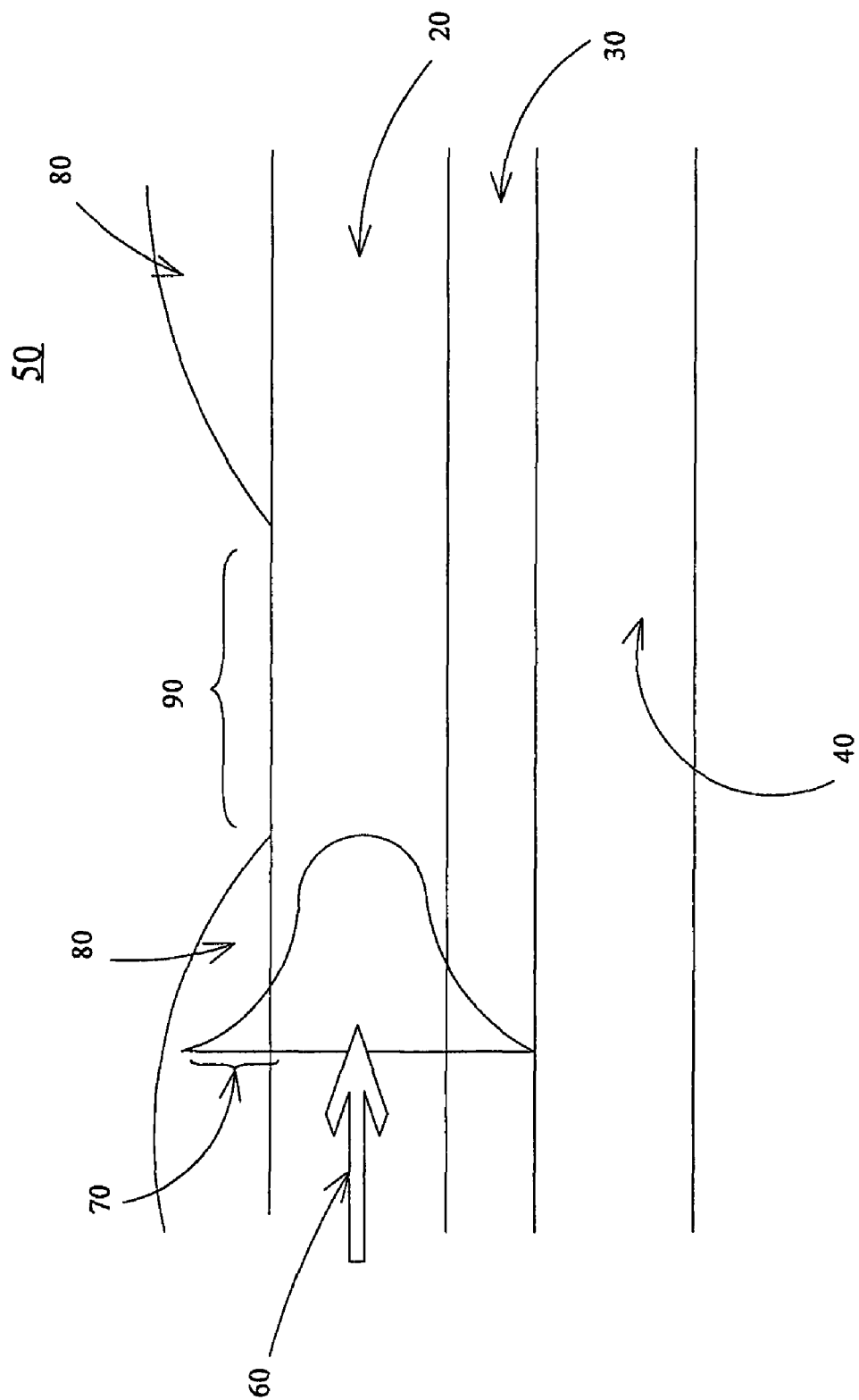
FIG. 5 is a side cut-away view of the sensor of FIG. 1 with a sensor window.

Experiments have shown that best results have been observed when silicon-on-insulator waveguides were used. Silicon photonic wire waveguides have been found to produce useful as the sensor elements in the sensor. For better results, a sensor window may be used to isolate the area where the waveguide core is exposed to the target molecules, to enable a comparison of the light travelling through the sensor waveguide with light travelling in an unexposed reference waveguide Referring to FIG. 5, such a sensor window is illustrated. An isolation layer 80 isolates the evanescent optical field 70 from the aqueous medium 50 and the molecular-interactions. A sensor window 90, an area in which the isolation layer is not present, exposes the evanescent optical field 70 to the medium 50 and thereby to the changed refractive index due to target-receptor molecule interactions. It should be noted that the isolation layer may be fabricated using well-known photosensitive polymer coatings normally used in the fabrication of semiconductor devices.

Figure 6A:
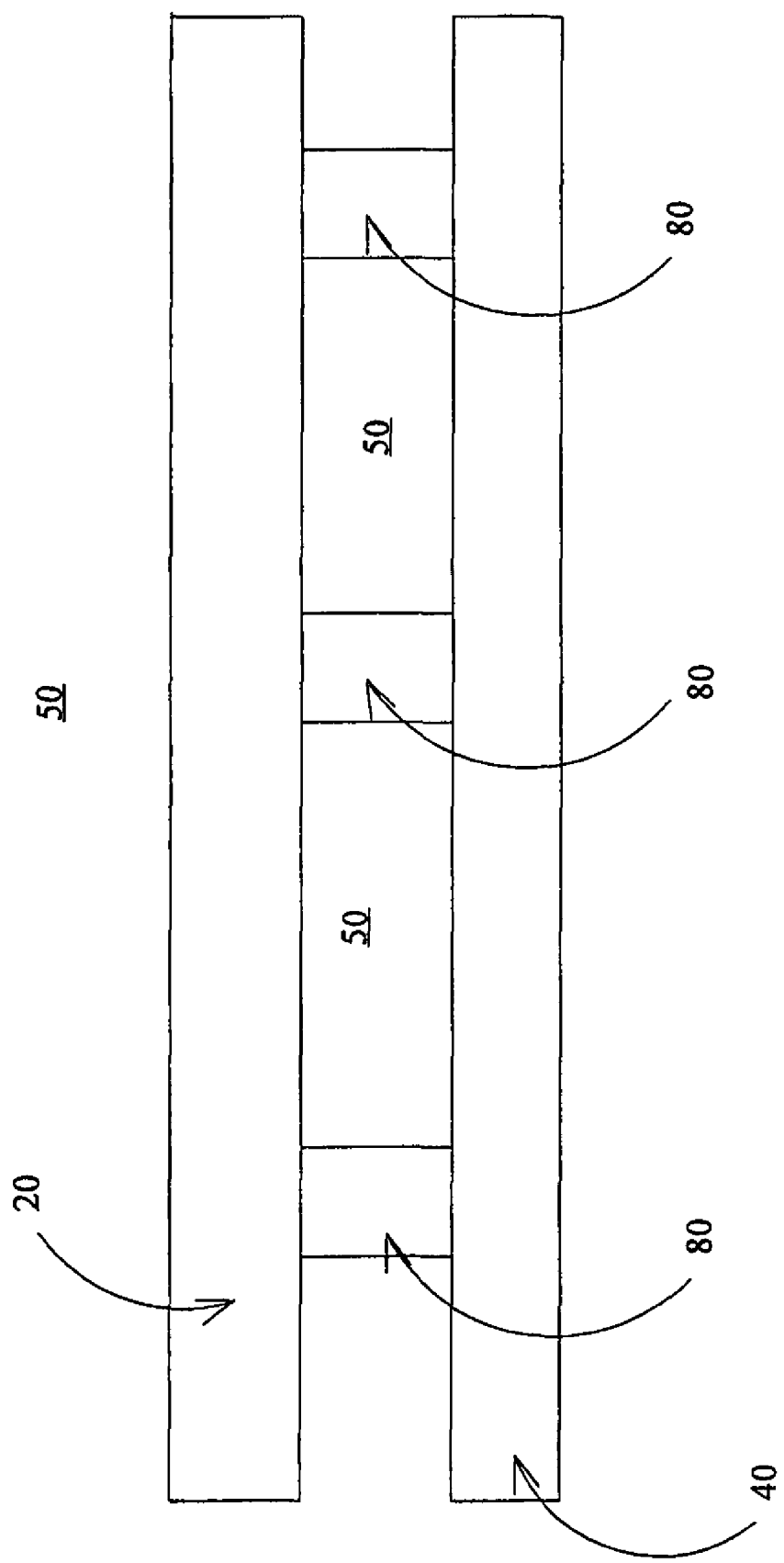
FIG. 6A illustrates a configuration of a sensor in which the silicon dioxide layer is provided as pillars supporting the waveguide.
Figure 6B:
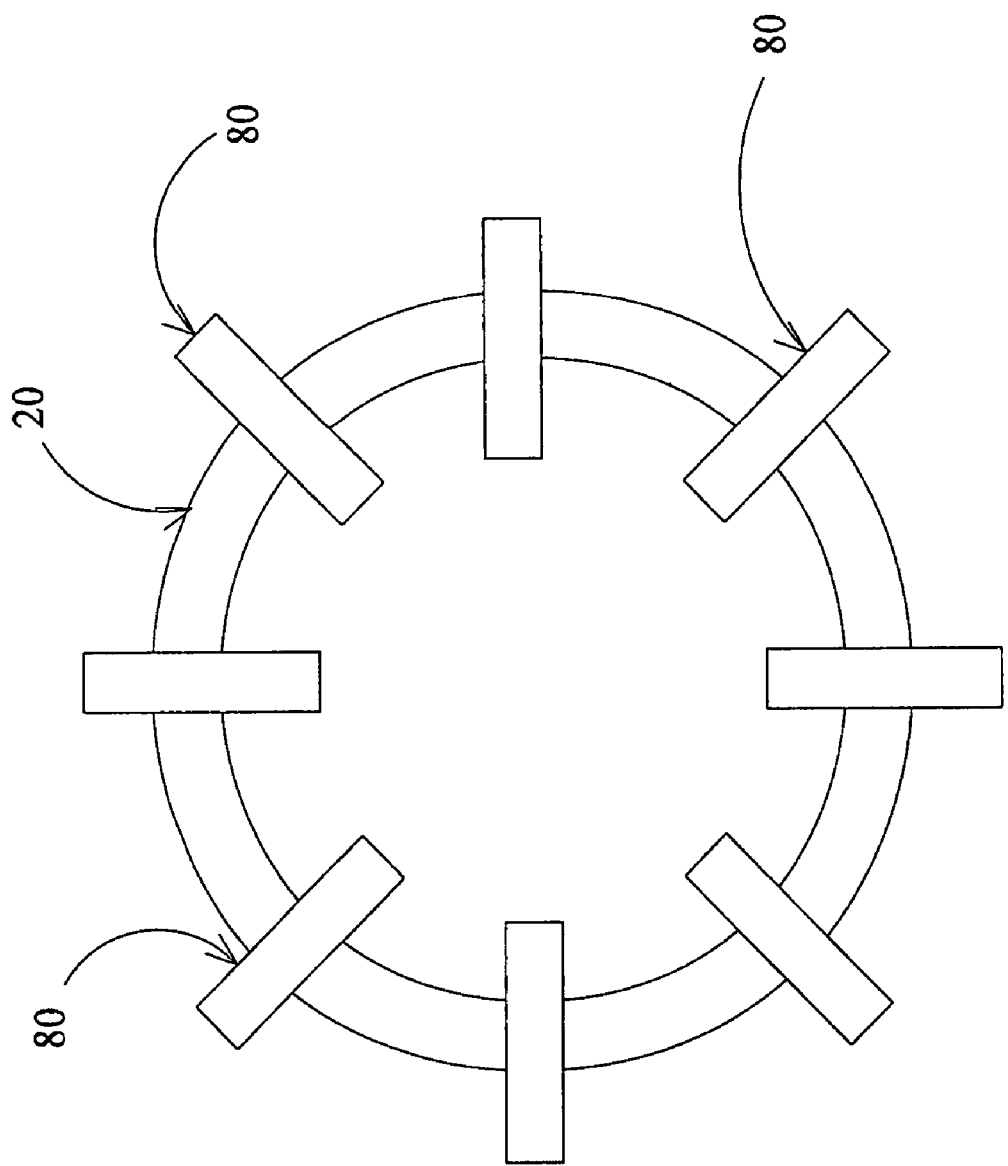
FIG. 6B illustrates a top-down view of a configuration of the sensor which can be used as a ring resonator.
Figure 7:
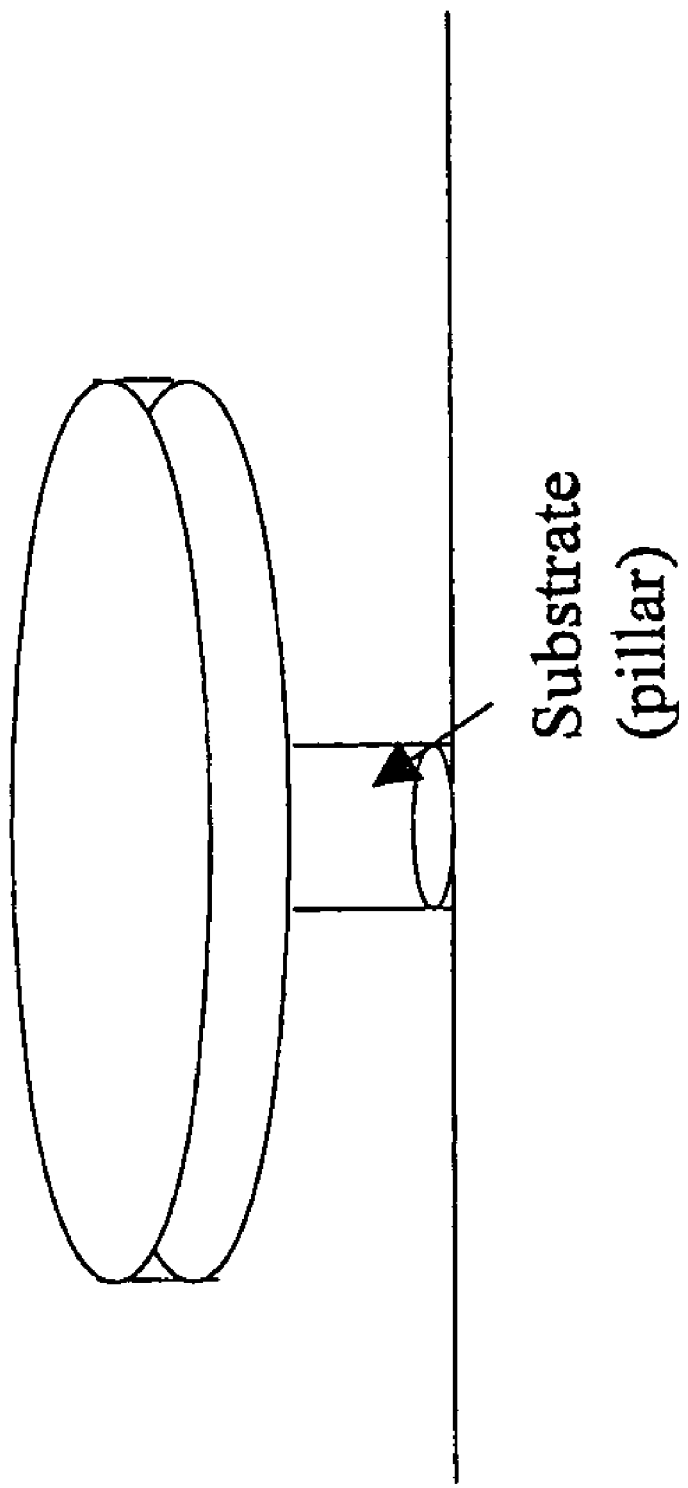
FIG. 7 illustrates a sensor configuration in which the sensor can be used as a microdisk resonator.

It should be noted that various configurations of the above noted sensor are possible. Referring to FIGS. 6A, 6B and 7, two different configurations are illustrated. FIGS. 6A and 6B illustrate a bridge configuration with the waveguide core being supported by pillars 80 of silicon oxide. This configuration allows the aqueous medium to surround the waveguide and thereby increase the surface area on which the molecular interactions can occur. Such a configuration can also be used to create a ring resonator as in FIG. 6B. In FIG. 7, a microdisk resonator can be configured using a single silicon oxide pillar 80 to support a microdisk waveguide sensor.

Experiments have also shown that better results have been achieved when the waveguides were thin as well as having a high contrast in terms of refractive index. Thus, better results were found when the contrast between the effective refractive index ($N_{eff}$) and the refractive index of the cladding was at a maximum. Also, it has been found that better results were achieved when the polarization of the light travelling in the waveguide was perpendicular to the active surface (the so-called TM mode). One material which produced acceptable results (thin waveguide, high index contrast, and TM mode) were silicon photonic wire waveguides. However, other materials may also provide equally acceptable results.

It should also be noted that the presence of a thin layer (i.e. the layer must be thinner than the extent of the evanescent field above the waveguide) of silicon dioxide between the waveguide and the medium containing the molecular interactions does not significantly degrade the performance (sensitivity) of the sensor. As such, a layer of silicon dioxide (i.e. glass) may be deposited on the waveguide.

Based on the above, silicon or other established glass biochip chemistries may be used in the production of the above noted sensor elements.

The invention claimed is:

1. A sensor for use in detecting molecules in a liquid or gas medium, the sensor comprising:
    a substrate layer,
    a light waveguide sensor element adjacent said medium,
    a lower cladding layer between said sensor element and said substrate layer wherein
    molecular interactions at the waveguide surface affect at least one characteristic of light travelling through said waveguide sensor element
    said sensor element comprises a thin, high refractive index contrast waveguide
    said sensor element is a silicon photonic wire waveguide,
    said light travelling through said sensor element is only polarized in one mode, and
    polarization of said light travelling through the sensor element is perpendicular to an active sensor surface.

2. A sensor according to claim 1 wherein said a portion of said sensor element is exposed to said liquid or gas medium through a sensor window in an isolation layer which isolates said sensor element from said liquid or gas medium.

3. A sensor according to claim 1 wherein said lower cladding layer comprises a layer of silicon dioxide.

4. A sensor according to claim 1 wherein said lower cladding layer comprises at least one pillar of silicon oxide supporting said sensor element on said substrate layer.

5. A sensor according to claim 1 wherein said sensor element comprises a ridge waveguide.

6. A sensor according to claim 1 wherein said sensor element comprises a channel waveguide.

7. A sensor according to claim 1 wherein said sensor element is configured as a straight waveguide.

8. A sensor according to claim 1 wherein said sensor element is configured as a resonator.

9. A sensor according to claim 1 wherein said sensor element is incorporated in a Mach-Zehnder interferometer.

10. A sensor according to claim 1 wherein said sensor further comprises a silicon dioxide layer between said medium and said sensor element.

11. A sensor according to claim 1 wherein said at least one characteristic of light comprises a speed of said light.

12. A method for detecting molecular interactions in an aqueous medium using a sensor having a light waveguide sensor element adjacent said aqueous medium, the method comprising:
   a) determining characteristics of light prior to said light entering said sensor element
   b) passing light through said sensor element
   c) determining characteristics of light after it has exited said sensor element
   d) comparing results of steps a) and c) to determine if changes in characteristics of said light occurred
   e) in the event said changes in characteristics occurred, measuring said changes wherein
      said sensor element comprises a thin, high refractive index contrast waveguide
      said sensor element is a silicon photonic wire waveguide, and
      said light travelling through said sensor element is only polarized in one mode, and
      polarization of said light travelling through the sensor element is perpendicular to an active sensor surface.

* * * * *

UNITED STATES PATENT AND TRADEMARK OFFICE
CERTIFICATE OF CORRECTION

PATENT NO. : 7,778,499 B2  
APPLICATION NO. : 11/898660  
DATED : August 17, 2010  
INVENTOR(S) : Xu et al.

Page 1 of 1

It is certified that error appears in the above-identified patent and that said Letters Patent is hereby corrected as shown below:

On the title page item (75) Inventors:

Siegfried Janz, Ottawa (CA); Pavel Cheben, Ottawa (CA); Andre Delage, Ottawa (CA); Adam Densmore, Orleans (CA); Dan-xia Xu, Ottawa (CA)

Should be corrected as follows:

(75) Inventors:

Dan-Xia Xu, Ottawa (CA); Adam Densmore, Orleans (CA); Andre Delage, Ottawa (CA); Pavel Cheben, Ottawa (CA); Siegfried Janz, Ottawa (CA)

Signed and Sealed this
Fourteenth Day of June, 2011

David J. Kappos
*Director of the United States Patent and Trademark Office*